US00PP22323P2

(12) United States Plant Patent
Talmadge

(10) Patent No.: US PP22,323 P2
(45) Date of Patent: Dec. 13, 2011

(54) ***IPOMOEA* PLANT NAMED 'IPOSGDEEPUR'**

(50) Latin Name: *Ipomoea batatas*
Varietal Denomination: IPOSGDEEPUR

(75) Inventor: Paul Talmadge, Orcutt, CA (US)

(73) Assignee: Floranova Service Corp

( * ) Notice: Subject to any disclaimer, the term of this patent is extended or adjusted under 35 U.S.C. 154(b) by 0 days.

(21) Appl. No.: 12/807,431

(22) Filed: Sep. 2, 2010

(51) Int. Cl.
*A01H 5/00* (2006.01)

(52) U.S. Cl. ..... Plt./226
(58) Field of Classification Search ..... Plt./226
See application file for complete search history.

*Primary Examiner* — Annette Para
(74) *Attorney, Agent, or Firm* — Cassandra Bright

(57) ABSTRACT

A new and distinct *Ipomoea* cultivar named 'IPOSGDEEPUR' is disclosed, characterized by deep purple-red, palmate shaped foliage, and a bush forming, non-vining habit. Additionally the new cultivar flowers under day neutral or short day conditions and produces many lateral branches, without pinching or chemical growth regulators. The new cultivar is an *Ipomoea*, typically suited for ornamental container and garden use.

1 Drawing Sheet

Figure 1:
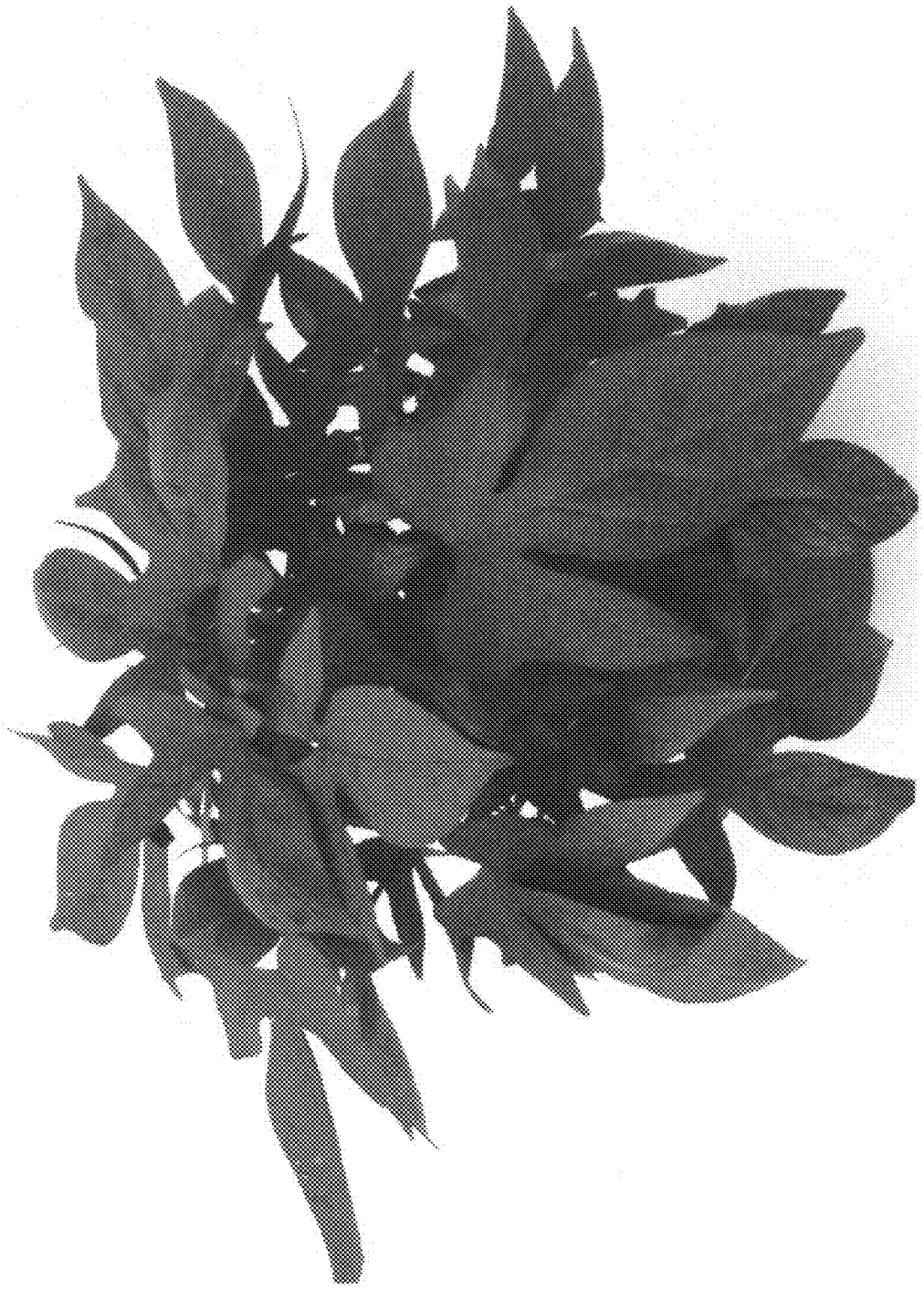

Latin name of the genus and species: *Ipomoea batatas.*
Variety denomination: 'IPOSGDEEPUR'.

BACKGROUND OF THE INVENTION

The new variety originated from a commercial breeding program under the direction of the inventor, Paul A. Talmadge. The crossing resulting in the new cultivar was made in Fall of 2007, with the seed parent, an unpatented, unnamed proprietary seedling and the pollen parent, also an unpatented, unnamed proprietary seedling. The new variety was discovered by the inventor in April of 2008 at a commercial greenhouse in Lompoc, Calif.

After selecting and isolating the new cultivar, asexual reproduction of the new cultivar 'IPOSGDEEPUR' was first performed in a commercial research greenhouse in Lompoc, Calif. during June of 2008. 'IPOSGDEEPUR' has since produced several generations and has shown that the unique features of this cultivar are stable and reproduced true to type. Asexual reproduction of the new variety is by vegetative cuttings.

SUMMARY OF THE INVENTION

The cultivar 'IPOSGDEEPUR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IPOSGDEEPUR.' These characteristics in combination distinguish 'IPOSGDEEPUR' as a new and distinct *Ipomoea* cultivar:

1. Deep purple-red foliage
2. Palmate foliage shape.
3. Bush forming habit, non-vining.
4. Very well branched, without pinching or chemical growth regulator use
5. Day length neutral, or short day flowering response.

PARENTAL COMPARISON

Plants of the new cultivar 'IPOSGDEEPUR' are similar to the seed parent in most horticultural characteristics. However, 'IPOSGDEEPUR' differs in producing foliage that is characteristically dark purple-red in color, whereas the seed parent has entirely purple foliage.

Plants of the new cultivar 'IPOSGDEEPUR' are similar to the pollen parent in most horticultural characteristics. However, 'IPOSGDEEPUR' produces a deep purple-red foliage, whereas the pollen parent has light green foliage. Additionally the pollen parent has a vining plant habit, with poor branches, compared to the mounded well branched habit of 'IPOSGDEEPUR.'

COMMERCIAL COMPARISON

Plants of the new cultivar 'IPOSGDEEPUR' are best compared to the commercial variety *Ipomoea batatas* 'Sweet Caroline Purple' U.S. Plant Pat. No. 14,912. Plants of 'IPOSGDEEPUR' are similar to plants of 'Sweet Caroline Purple' in most horticultural characteristics, however, plants of 'IPOSGDEEPUR' have, dark purple-red foliage, whereas 'Sweet Caroline Purple' has purple foliage. Additionally, 'IPOSGDEEPUR' flowers under day length neutral or short day conditions, whereas 'Sweet Caroline Purple' is long day flowering.

BRIEF DESCRIPTION OF THE PHOTOGRAPH

The accompanying photograph in FIG. 1 illustrates in full color a typical plant of 'IPOSGDEEPUR' grown in a greenhouse in Lompoc, Calif. This plant is approximately 8 weeks old, from an unrooted cutting, shown in a 6 inch pot pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Formula Guide Solid Matte, First Edition 2000-

2001, except where general terms of ordinary dictionary significance are used. The following observations and measurements describe 'IPOSGDEEPUR' plants grown during the Summer months in a greenhouse in Lompoc, Calif., under bright, unshaded conditions. Average day temperatures were approximately 26° C. and the average night temperature was approximately 18° C. No artificial light, photoperiodic treatments or chemical treatments were given to the plants. Measurements and numerical values represent averages of typical plant types.

Botanical classification: *Ipomoea batatas* 'IPOSGDEEPUR'

Age of the plant described: Approximately 8 weeks from an unrooted cutting.

Container size of the plant described: 6 inch commercial container.

PROPAGATION

*Propagation method.*—Terminal cuttings.

*Time to develop roots suitable for transplanting.*—Summer-about six days at an average temperature of 24° C.; Winter-about ten days at an average temperature of 24° C.

*Root description.*—Thick, fleshy.

*Tuber description.*—None observed.

PLANT

Growth habit: Compact, upright and mounding

Height: Measured from top of soil line of pot, approximately 22 cm

Plant spread: Approximately 45 cm

Growth rate: Rapid

Branching characteristics: Very free branching, alternate occurring.

Primary lateral branches:

*Length.*—A range between 8 to 9 cm.

*Diameter.*—Approximately 0.5 to 0.6 cm.

*Texture.*—Glabrous, with occasional hairs seen with a hand lens.

*Color.*—Pantone 505C at base, Pantone 383C at tip.

*Strength.*—Strong.

*Internode length.*—A range between 0.5-1.5 cm.

*Adventitious roots at nodes.*—Non observed.

Secondary lateral branches: Not observed, only primary lateral branches on an 8 week old plant.

New shoot growth characteristics:

*Color.*—Pantone 385C.

*Aspect.*—Upright.

*Texture.*—Glabrous.

FOLIAGE

Leaf:

*Arrangement.*—Alternate, simple.

*Average length.*—Approximately 13 cm.

*Average width.*—Approximately 11 cm.

*Shape of blade.*—Palmate with 3 to 5 lobes; 3 lobes on newly rooted cuttings, 5 lobes on more mature stems.

*Apex.*—Acuminate.

*Base.*—Cordate to auriculate.

*Margin.*—Entire, with tiny hairs visible with a hand lens.

*Aspect.*—Folded upwards slightly along midrib at base, flattening to curving downward toward apex.

*Texture of top surface.*—Glabrous.

*Texture of bottom surface.*—Glabrous.

*Quantity of leaves per lateral branch.*—Approximately 10.

Color:

*Young foliage upper side.*—Pantone 385C.

*Young foliage under side.*—Pantone 385C.

*Mature foliage upper side.*—Pantone 5185C.

*Mature foliage under side.*—Pantone 5195C.

Venation:

*Type.*—Palmate: arcuate to reticulate at base.

*Venation color upper side.*—Pantone 505C.

*Venation color under side.*—Pantone 505C.

Petiole:

*Length.*—Longest petioles approximately 13 cm.

*Diameter.*—Approximately 0.5 cm at base, 0.3 cm at top.

*Texture.*—Glabrous.

*Color.*—Pantone 505C.

*Strength.*—Strong.

*Aspect.*—Upright to slightly curved.

FLOWER

None observed.

OTHER CHARACTERISTICS

Seeds and fruits: No seeds/fruits observed.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 40° C.

What is claimed is:

1. A new and distinct cultivar of *Ipomoea batatas* plant named 'IPOSGDEEPUR' as herein illustrated and described.

* * * * *